United States Patent
Yang et al.

(10) Patent No.: US 11,174,237 B2
(45) Date of Patent: *Nov. 16, 2021

(54) 2-[4-(MEIHYLAMINOMETHYL)PHENYL]-5-FLUORO- BENZOFURAN-7-CARBOXAMIDE HYDROCHLORIDE POLYMORPH, PREPARATION METHOD THEREFOR AND APPLICATION THEREOF

(71) Applicants: SHANGHAI INSTITUTE OF MATERIA MEDICA, CHINESE ACADEMY OF SCIENCES, Shanghai (CN); FUKANG (SHANGHAI) HEALTH TECHNOLOGY CO., LTD., Shanghai (CN)

(72) Inventors: Chunhao Yang, Shanghai (CN); Zehong Miao, Shanghai (CN); Cun Tan, Shanghai (CN); Xiajuan Huan, Shanghai (CN); Jian Ding, Shanghai (CN); Yi Chen, Shanghai (CN)

(73) Assignees: SHANGHAI INSTITUTE OF MATERIA MEDICA, CHINESE ACADEMY OF SCIENCES, Shanghai (CN); FUKANG (SHANGHAI) HEALTH TECHNOLOGY CO., LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/623,297
(22) PCT Filed: May 31, 2018
(86) PCT No.: PCT/CN2018/089222
§ 371 (c)(1),
(2) Date: Dec. 16, 2019
(87) PCT Pub. No.: WO2018/228205
PCT Pub. Date: Dec. 20, 2018

(65) Prior Publication Data
US 2020/0172502 A1    Jun. 4, 2020

(30) Foreign Application Priority Data
Jun. 14, 2017  (CN) .......................... 201710449281.2

(51) Int. Cl.
C07D 307/84    (2006.01)
(52) U.S. Cl.
CPC ........ *C07D 307/84* (2013.01); *C07B 2200/13* (2013.01)

(58) Field of Classification Search
CPC .................................................. C07D 307/84
See application file for complete search history.

(56) References Cited

U.S. PATENT DOCUMENTS 9,533,965 B2 *  1/2017  Yang ........................ A61P 43/00
2015/0018542 A1 *  1/2015  Yang ..................... C07C 67/307
540/575

FOREIGN PATENT DOCUMENTS

| CN | 102627620 A | 8/2012 | |
|---|---|---|---|
| WO | 2013/117120 A1 | 8/2013 | |
| WO | WO-2020119772 A1 * | 6/2020 | ........... C07D 307/81 |

OTHER PUBLICATIONS

Morissette; Advanced Drug Delivery Reviews 2004, 56, 275-300. (Year: 2004).*
He; Oncotarget. 2017, 8, 4156-4168. Published: Dec. 1, 2016. (Year: 2016).*
Jin, Qiu et al; "Design, Synthesis and Activity of Benzofuran-7-carboxamide Poly(ADP-ribose)-polymerase Inhibitors"; Chinese Journal of Organic Chemistry; vol. 33, No. (3); Mar. 31, 2013; ISSN: 0253-2786, pp. 590-595.

* cited by examiner

*Primary Examiner* — Daniel R Carcanague
(74) *Attorney, Agent, or Firm* — Novick, Kim & Lee, PLLC; Bin Lu; Zhi Yang Xue

(57) ABSTRACT

Disclosed are a 2-[4-(methylaminomethyl)phenyl]-5-fluoro-benzofuran-7-carboxamide hydrochloride polymorph, a preparation method therefor and an application thereof. Specifically, disclosed are three crystalline forms, i.e., crystalline forms A, B, and C, of 2-[4-(methylaminomethyl) phenyl]-5-fluoro-benzofuran-7-carboxamide hydrochloride (formula I), preparation methods for the three crystalline forms, and use of the three crystalline forms in preparation of drugs.

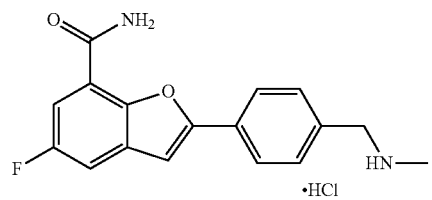

8 Claims, 15 Drawing Sheets

2-[4-(METHYLAMINOMETHYL)PHENYL]-5-FLUORO- BENZOFURAN-7-CARBOXAMIDE HYDROCHLORIDE POLYMORPH, PREPARATION METHOD THEREFOR AND APPLICATION THEREOF

TECHNICAL FIELD

The present invention belongs to the category of medicinal chemistry, and specifically relates to polymorphs of 2-[4-(methylaminomethyl)phenyl]-5-fluoro-benzofuran-7-carboxamide hydrochloride and a preparation method and use thereof in the preparation of a medicine.

BACKGROUND ART

Different crystal forms of a compound may have different properties, such as solubility, dissolution rate, suspension stability, stability during milling, vapor pressure, optical and mechanical properties, hygroscopicity, crystal size, filtration performance, drying, density, melting point, degradation stability, stability to prevent phase change to other crystal forms, color and even chemical reactivity, etc. More importantly, the different crystal forms of a small molecule compound may change its dissolution, dissolution performance, pharmacokinetics and bioavailability, which will affect the efficacy and safety performance of a drug. Therefore, the polymorph of small-molecule drugs should be fully considered during the development process. Therefore, research and control on crystal form has become one of the important research contents in the process of small molecule drug development.

WO2013117120 disclosed a PARP selective inhibitor with pharmaceutical value, in which an example of a series of specifically described inhibitors (see Example 21 on page 37) is 2-[4-(methylaminomethyl)phenyl]-5-fluoro-benzofuran-7-carboxamide hydrochloride (hereinafter referred to as mefurapine hydrochloride), with a structure as shown in Formula I:

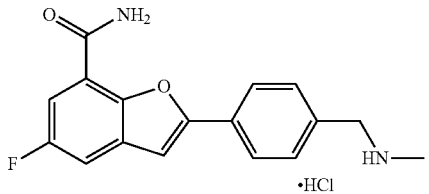

According to the method disclosed in WO2013117120, the compound was characterized by $^1$HMR analysis and/or measurement of melting point. In the prior art, different crystal forms of mefurapine hydrochloride were not described, and any characterization of a specific crystal form and the preparation method used to obtain a specific crystal form have not been described. Different crystal forms of mefurapine hydrochloride may change its dissolution, dissolution performance, pharmacokinetics and bioavailability, and then affect the efficacy and safety of the drug. Therefore, for the large-scale preparation of mefurapine hydrochloride, it is important to know if there are different crystal forms of this compound (also often referred to as polymorphs, or pseudopolymorphs in the case of solvent encapsulation), how to obtain them, and how its characteristic performance is.

SUMMARY OF THE INVENTION

In view of the above background, the present invention discloses various crystal forms of mefurapine hydrochloride, and characterization, preparation method as well as use thereof. Therefore, the technical problem to be solved by the present invention is to provide a polymorph of mefurapine hydrochloride, which provides technical support for further development of mefurapine hydrochloride.

In the first aspect of the present invention, it provides a polymorph of 2-[4-(methylaminomethyl)phenyl]-5-fluoro-benzofuran-7-carboxamide hydrochloride as shown in Formula I.

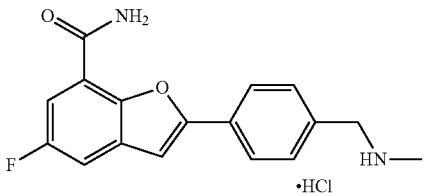

In another preferred embodiment, the polymorph is 2-[4-(methylaminomethyl)phenyl]-5-fluoro-benzofuran-7-carboxamide hydrochloride crystal form A, and the powder diffraction pattern thereof comprises 3 or more 2θ values selected from the group consisting of: 6.49±0.1°, 12.625±0.1°, 15.271±0.1°, 20.727±0.1°, 22.933±0.1°, 23.913±0.1°, 25.139±0.1°, 25.618±0.1°, 26.082±0.1°, 27.084±0.1°, 27.406±0.1°, and 28.828±0.1°.

In another preferred embodiment, the crystal form a further has one or more characteristics selected from the group consisting of:

(1) the crystal form A has a DSC spectrum substantially as shown in FIG. 1b;
(2) the crystal form A has an infrared spectrum substantially as shown in FIG. 1c;
(3) the crystal form A has a TG spectrum substantially as shown in FIG. 1d; and
(4) the crystal form A has a Raman spectrum substantially as shown in FIG. 1e.

In another preferred embodiment, the polymorph is 2-[4-(methylaminomethyl)phenyl]-5-fluoro-benzofuran-7-carboxamide hydrochloride crystal form B, and the powder diffraction pattern thereof comprises 3 or more 2θ values selected from the group consisting of: 6.145±0.1°, 10.318±0.1°, 12.459±0.1°, 14.914±0.1°, 20.806±0.1°, 22.832±0.1°, 23.295±0.1°, 24.996±0.1°, 25.198±0.1°, 25.481±0.1°, 26.787±0.1°, 27.285±0.1°, 28.003±0.1°, and 29.59±0.1°.

In another preferred embodiment, the crystal form B further has one or more characteristics selected from the group consisting of:

(1) the crystal form B has a DSC pattern substantially as shown in FIG. 2b;
(2) the crystal form B has an infrared spectrum substantially as shown in FIG. 2c;
(3) the crystal form B has a TG pattern substantially as shown in FIG. 2d; and
(4) the crystal form B has a Raman spectrum substantially as shown in FIG. 2e.

In another preferred embodiment, the polymorph is 2-[4-(methylaminomethyl)phenyl]-5-fluoro-benzofuran-7-carboxamide hydrochloride crystal form C, and the powder diffraction pattern thereof comprises 3 or more 2θ values selected from the group consisting of: 10.306±0.1°, 12.666±0.1°, 15.312±0.1°, 17.436±0.1°, 18.918±0.1°, 20.748±0.1°, 22.974±0.1°, 24.553±0.1°, 25.238±0.1°, 26.241±0.1°, 29.336±0.1°, 32.739±0.1°, 33.738±0.1°, 34.118±0.1°, 35.204.

In another preferred embodiment, the crystal form C further has one or more characteristics selected from the group consisting of:

(1) the crystal form C has a DSC pattern substantially as shown in FIG. 3b;

(2) the crystal form C has an infrared spectrum substantially as shown in FIG. 3c;

(3) the crystal form C has a TG pattern substantially as shown in FIG. 3d; and (4) the crystal form C has a Raman spectrum substantially as shown in FIG. 3e.

In the second aspect of the present invention, it provides a method for preparing the polymorph of 2-[4-(methylaminomethyl)phenyl]-5-fluoro-benzofuran-7-carboxamide hydrochloride according to the first aspect of the present invention, comprising the steps:

(i) dissolving 2-[4-(methylaminomethyl)phenyl]-5-fluoro-benzofuran-7-carboxamide hydrochloride crystal form A in an alcohol at 0° C. to 80° C. to form an alcohol solution containing 2-[4-(methylaminomethyl)phenyl]-5-fluoro-benzofuran-7-carboxamide hydrochloride;

(ii) adding an organic solvent dropwise to the alcohol solution of step i), stirring, standing, and precipitating crystals; and (iii) isolating and drying the precipitated crystals to obtain 2-[4-(methylaminomethyl)phenyl]-5-fluoro-benzofuran-7-carboxamide hydrochloride crystal form B;

wherein said alcohol is selected from the group consisting of: methanol, ethanol, propanol, tert-butanol, butanol, octanol, pentanol, hexanol, heptanol, decanol, or a combination thereof; the organic solvent is selected from the group consisting of: butanone, methyl tert-butyl ether, isopropyl acetate, or a combination thereof;

or the preparation method includes the steps of:

(a) dissolving 2-[4-(methylaminomethyl)phenyl]-5-fluoro-benzofuran-7-carboxamide hydrochloride crystal form A in an alcohol or an alcohol-water system at 0° C. to 80° C. to form an alcohol solution or an alcohol-water solution containing 2-[4-(methylaminomethyl)phenyl]-5-fluoro-benzofuran-7-carboxamide hydrochloride;

(b) adjusting the pH of the alcohol solution or the alcohol-water solution of step a) to be acidic with hydrochloric acid, stirring at room temperature, standing, and precipitating crystals; and (c) separating and drying the precipitated crystals to obtain 2-[4-(methylaminomethyl)phenyl]-5-fluoro-benzofuran-7-carboxamide hydrochloride crystal form C;

wherein said alcohol-water system is selected from the group consisting of methanol-water, ethanol-water, propanol-water, tert-butanol-water, butanol-water, octanol-water, pentanol-water, hexanol-water, heptanol-water or decanol-water.

In another preferred embodiment, the alcohol is methanol or ethanol, preferably ethanol.

In another preferred embodiment, the organic solvent is butanone or methyl tert-butyl ether, preferably butanone.

In another preferred embodiment, the alcohol-water system is methanol-water or ethanol-water, and preferably ethanol-water.

In another preferred embodiment, the pH of the alcohol or the alcohol-water solution of step a) is adjusted by hydrochloric acid to be 1 to 5, preferably the pH is 2 to 4, and more preferably the pH is 2.

In another preferred embodiment, the precipitated crystals are dried at 25° C. to 100° C.

In the third aspect of the present invention, it provides a pharmaceutical composition comprising a pharmaceutically effective dose of the polymorph of 2-[4-(methylaminomethyl)phenyl]-5-fluoro-benzofuran-7-carboxamide hydrochloride according to the first aspect of the present invention, and a pharmaceutically acceptable excipient or carrier.

In the fourth aspect of the present invention, it provides the use of the polymorph of 2-[4-(methylaminomethyl)phenyl]-5-fluoro-benzofuran-7-carboxamide hydrochloride according to the first aspect of the present invention or the composition according to the third aspect of the present invention for preparing a drug for treating and/or preventing diseases related to poly (ADP-ribose polymerase) (PARP).

In another preferred embodiment, the diseases include: tumor, inflammation, cardiovascular disease, diabetes, rheumatoid arthritis, endotoxic shock, and stroke.

In another preferred embodiment, the tumor includes: a tumor in which BRCA1 or BRCA2 is deleted or mutated.

In another preferred embodiment, the tumor includes: ovarian cancer, breast cancer, prostate cancer, gastric cancer, pancreatic cancer, cervical cancer, glioma, and Ewing's sarcoma.

In another preferred embodiment, the drugs include anti-tumor drugs and/or anti-inflammatory drugs.

It should be understood that in the present invention, any of the technical features specifically described above and below (such as in the Examples) can be combined with each other, which will not redundantly be described one by one herein.

DETAILED DESCRIPTION OF THE INVENTION

Figure 1A:
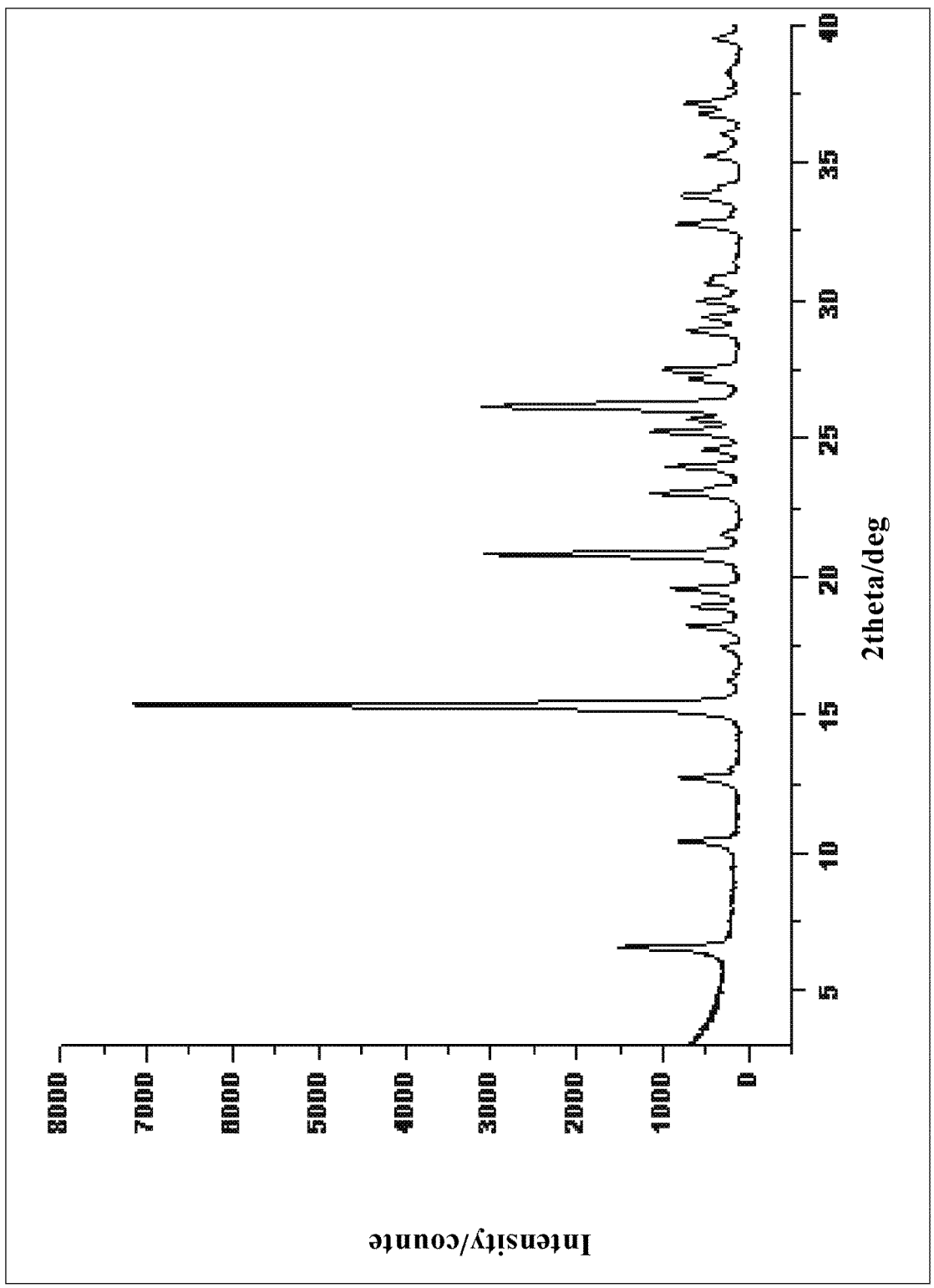
FIG. 1a is an X-ray powder diffraction (XRPD) pattern of mefurapine hydrochloride crystal form A.

After extensive and in-depth research, the present inventors have unexpectedly discovered three new polymorphs of mefurapine hydrochloride, and the preparation process is simple, efficient, and repeatable, and can realize large-scale industrial production. On above basis, the present invention has been completed.

Terms

Unless otherwise defined, all technical and scientific terms used herein have the same meaning as commonly understood by one of ordinary skill in the art to which this invention belongs.

As used herein, when used in reference to a particular recited value, the term "about" means that the value can vary by no more than 1% from the recited value. For example, as used herein, the expression "about 100" includes all values between 99 and 101 (e.g., 99.1, 99.2, 99.3, 99.4, etc.).

For a characteristic diffraction peak represented by a 2θ angle, the term "about" means that the listed value varies by no more than 0.2°, for example, about X °, it means X±0.2°, preferably X±0.1°.

As used herein, the terms "contains" or "includes (comprises)" may be open ended, semi-close ended and close ended. In other words, the terms also include "consisting essentially of" or "consisting of".

As used herein, the term "room temperature" generally refers to 4-30° C., preferably 20±5° C.

As used herein, the term "pharmaceutically acceptable ingredient" refers to a substance that is suitable for use in humans and/or animals without excessive adverse side effects (such as toxicity, irritation, and allergies), that is, with a reasonable benefit/risk ratio.

As used herein, the term "effective amount" refers to an amount of a therapeutic agent to treat, alleviate or prevent a target disease or condition, or an amount that exhibits a detectable therapeutic or preventive effect. The exact effective amount for a subject depends on the subject's size and health, the nature and extent of the condition, and the chosen therapeutic agent and/or combination of therapeutic agents. Therefore, it is not useful to specify an accurate effective amount in advance. However, for a given condition, a routine experiment can be used to determine the effective amount, which can be judged by the clinician.

Crystallization

A solution can be manipulated so that the solubility limit of a compound of interest can be exceeded, thereby completing crystallization on a production scale. This can be done in a number of ways, for example by dissolving the compound at a relatively high temperature and then cooling the solution below the saturation limit, or reducing the volume of the liquid by boiling, atmospheric evaporation, vacuum drying, or some other methods. The solubility of a compound of interest can be reduced by adding an anti-solvent or a solvent in which the compound has a low solubility, or a mixture of such solvents. Another option is to adjust the pH to reduce solubility. For a detailed description of crystallization, see Crystallization, 3rd Edition, J W Mullens, Butterworth-Heineman Ltd., 1993, ISBN 0750611294.

If it is desired that the salt formation and crystallization occur at the same time, and if the salt is less soluble in the reaction medium than the starting material, then the addition of a suitable acid or base can result in direct crystallization of the desired salt. Also, in a medium where the final desired form is less soluble than the reactants, the completion of the synthetic reaction allows the final product to crystallize directly.

Optimization of the crystallization may include seeding the crystals in the desired form as crystal seed in the crystallization medium. In addition, a combination of the above strategies is adopted in many crystallization methods. One example is to dissolve the compound of interest in a solvent at a high temperature, and then an appropriate volume of anti-solvent is added in a controlled manner so that the system is just below the saturation level. At this point, a crystal seed in the desired form can be added (and the integrity of the crystal seed is maintained) and the system is cooled to complete the crystallization.

Polymorphs of the Invention

The polymorph of mefurapine hydrochloride according to the present invention includes three crystal forms: crystal form A, crystal form B, and crystal form C.

Crystal Form A

The powder X-ray diffraction pattern of the mefurapine hydrochloride crystal form A of the present invention has obvious characteristic absorption peaks at diffraction angles (2θ) of approximately 6.49, 12.625, 15.271, 20.727, 22.933, 23.913, 25.139, 25.618, 26.082, 27.084, 27.406, 28.828.

The X-ray powder diffraction pattern of the mefurapine hydrochloride crystal form A is substantially consistent with FIG. 1a; the DSC spectrum, and the infrared spectrum, the TG spectrum, and the Raman spectrum are substantially consistent with FIGS. 1b, 1c, 1d, and 1e.

Figure 1B:
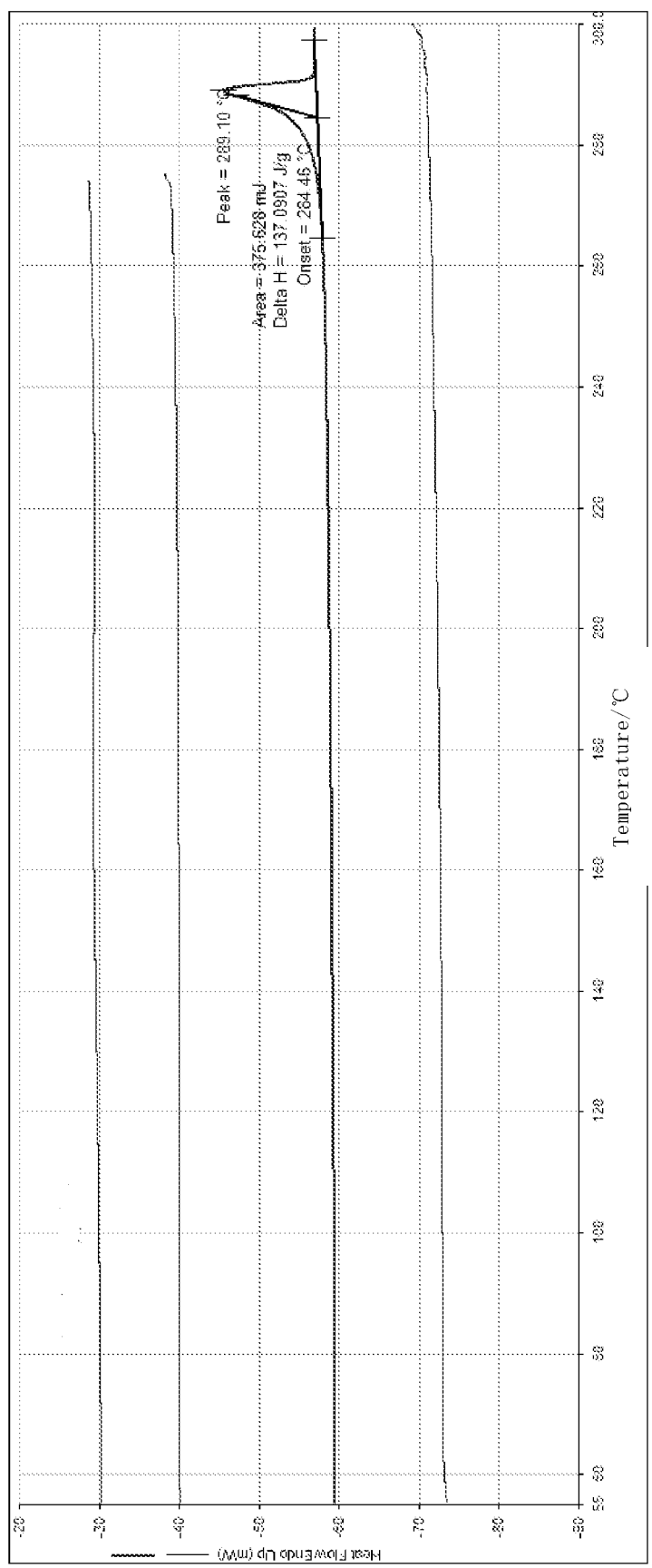
FIG. 1b is a DSC spectrum of mefurapine hydrochloride crystal form A.

It can be seen from FIG. 1b that the crystal form A has a characteristic endothermic peak in the range of about 280-300° C.

Figure 1C:
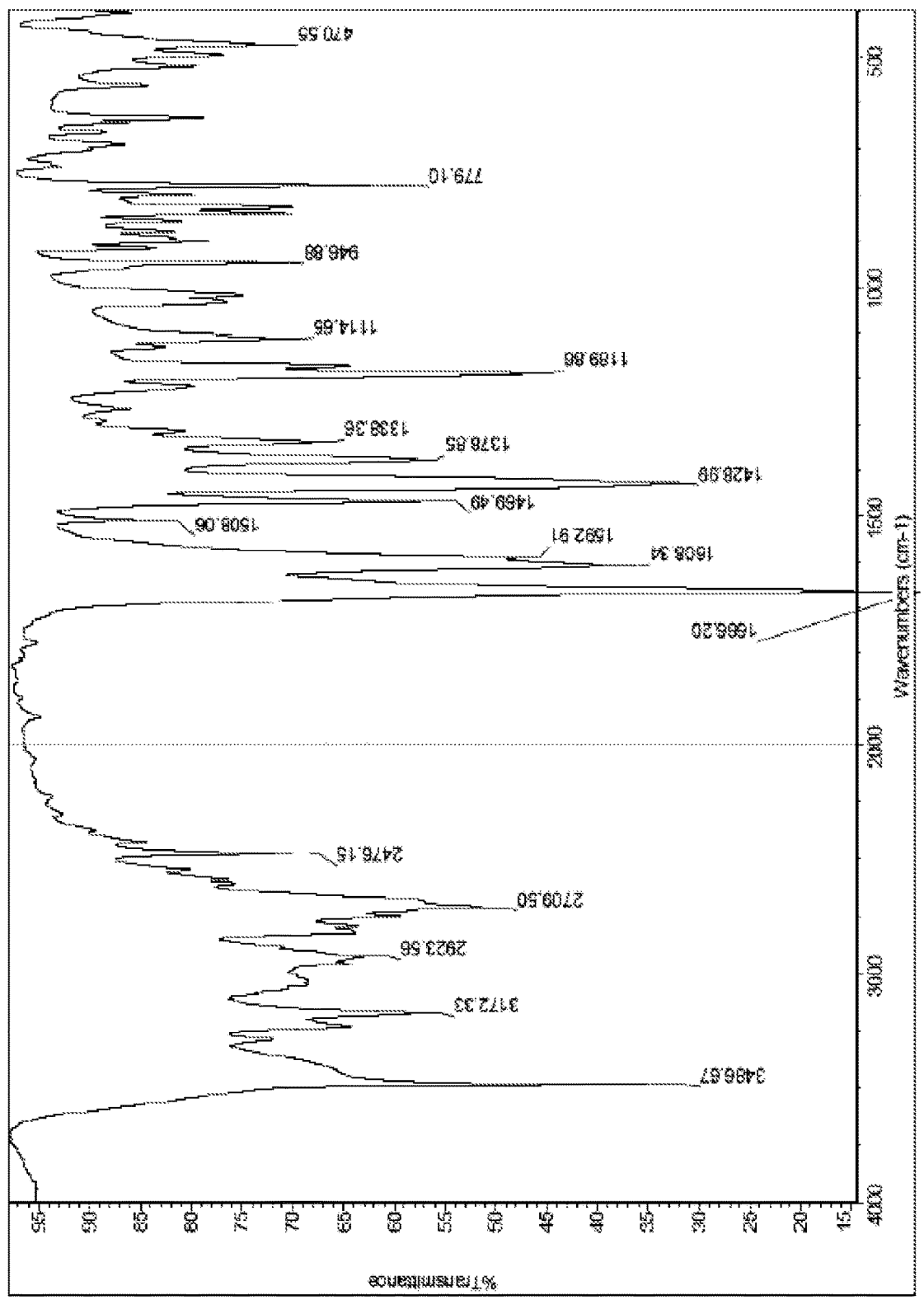
FIG. 1c is an infrared (IR) spectrum of mefurapine hydrochloride crystal form A.

It can be seen from FIG. 1c that, in the infrared spectrum of the crystal form A, there are characteristic peaks at least at 3486 $cm^{-1}$, 3172 $cm^{-1}$, 2923 $cm^{-1}$, 2709 $cm^{-1}$, 2476 $cm^{-1}$, 1666 $cm^{-1}$, 1608 $cm^{-1}$, 1592 $cm^{-1}$, 1469 $cm^{-1}$, 1428 $cm^{-1}$, 1378 $cm^{-1}$, 1,338 $cm^{-1}$, 1189 $cm^{-1}$, 1114 $cm^{-1}$, 946 $cm^{-1}$, 779 $cm^{-1}$, and 470 $cm^{-1}$, and the error range is ±2 $cm^{-1}$.

Figure 1D:
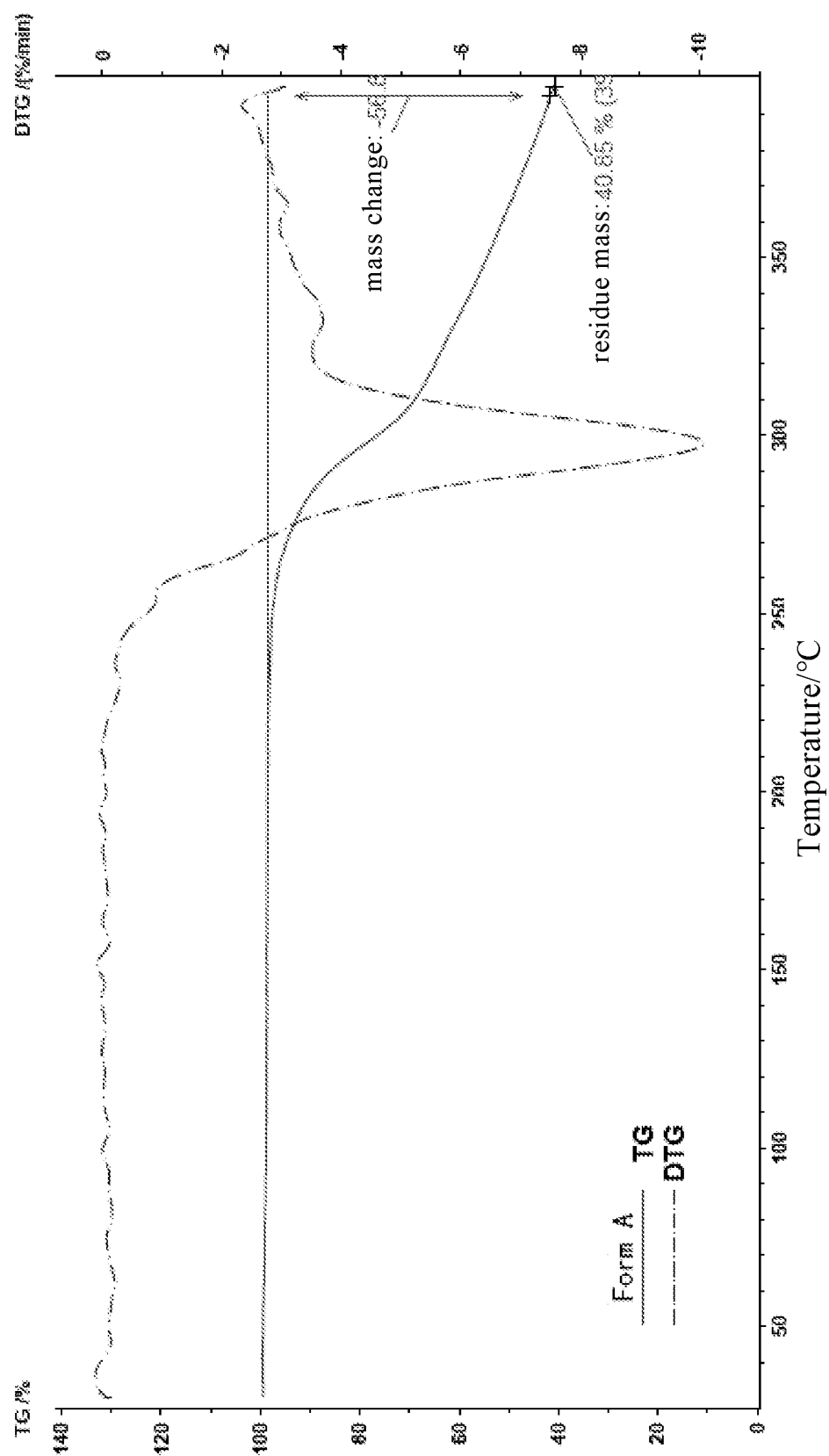
FIG. 1d is a TG spectrum of mefurapine hydrochloride crystal form A.

It can be concluded from FIG. 1d that the crystal form A begins to decompose at 250±20° C. according to the thermogravimetric analysis.

Crystal Form B

The powder X-ray diffraction pattern of the mefurapine hydrochloride crystal form B of the present invention has obvious characteristic absorption peaks at diffraction angles (2θ) of approximately 6.145, 10.318, 12.459, 14.914, 20.806, 22.832, 23.295, 24.996, 25.198, 25.481, 26.787, 27.285, 28.003 and 29.59.

Figure 2A:
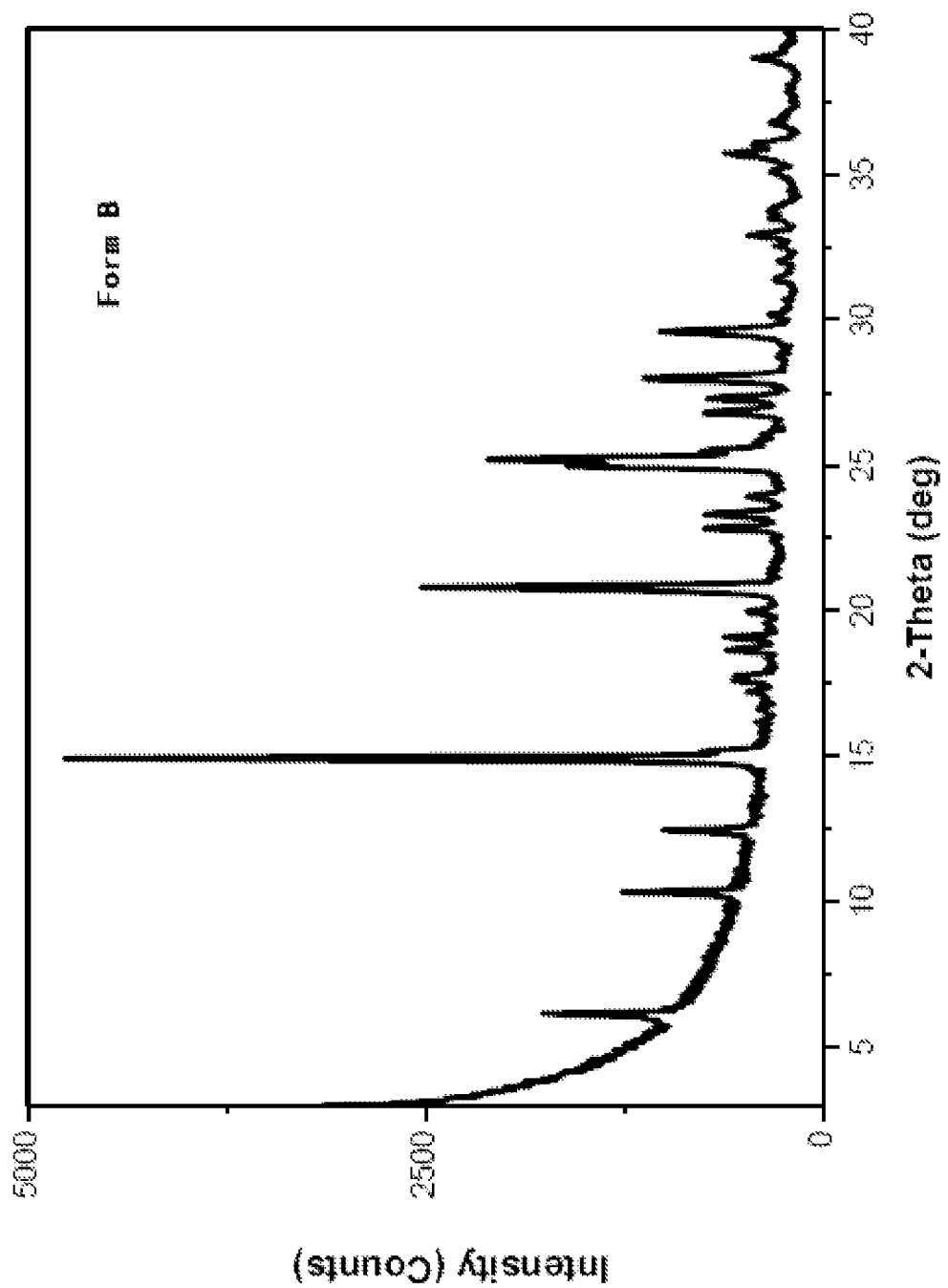
FIG. 2a is an X-ray powder diffraction (XRD) pattern of mefurapine hydrochloride crystal form B.

The X-ray powder diffraction pattern of the mefurapine hydrochloride crystal form B is substantially consistent with FIG. 2a; and the DSC spectrum, the infrared spectrum, the TG spectrum, and the Raman spectrum are substantially consistent with FIGS. 2b, 2c, 2d, and 2e.

Figure 2B:
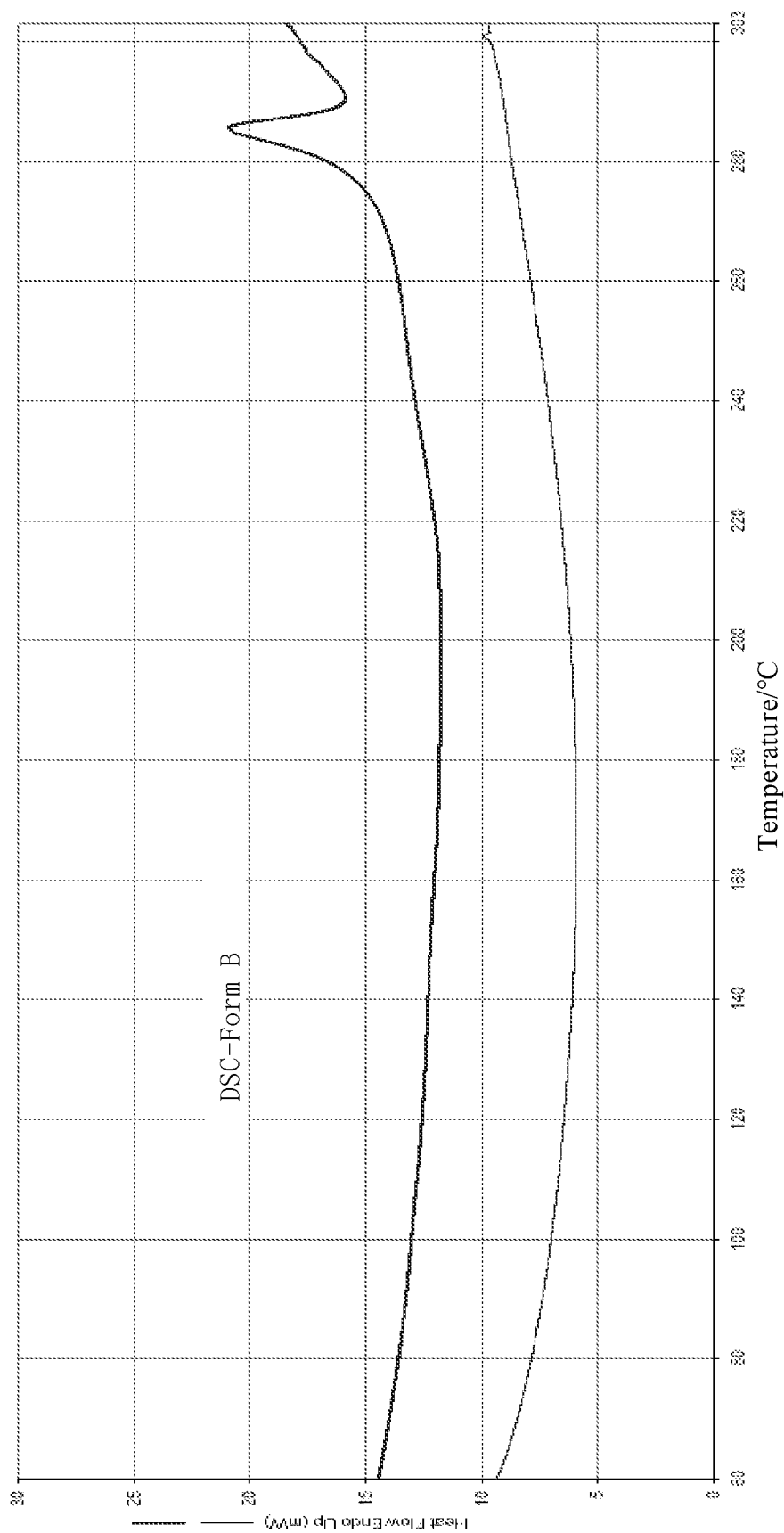
FIG. 2b is a DSC spectrum of mefurapine hydrochloride crystal form B.

It can be seen from FIG. 2b that the crystal form B has a characteristic endothermic peak in the range of about 280-300° C.

Figure 2C:
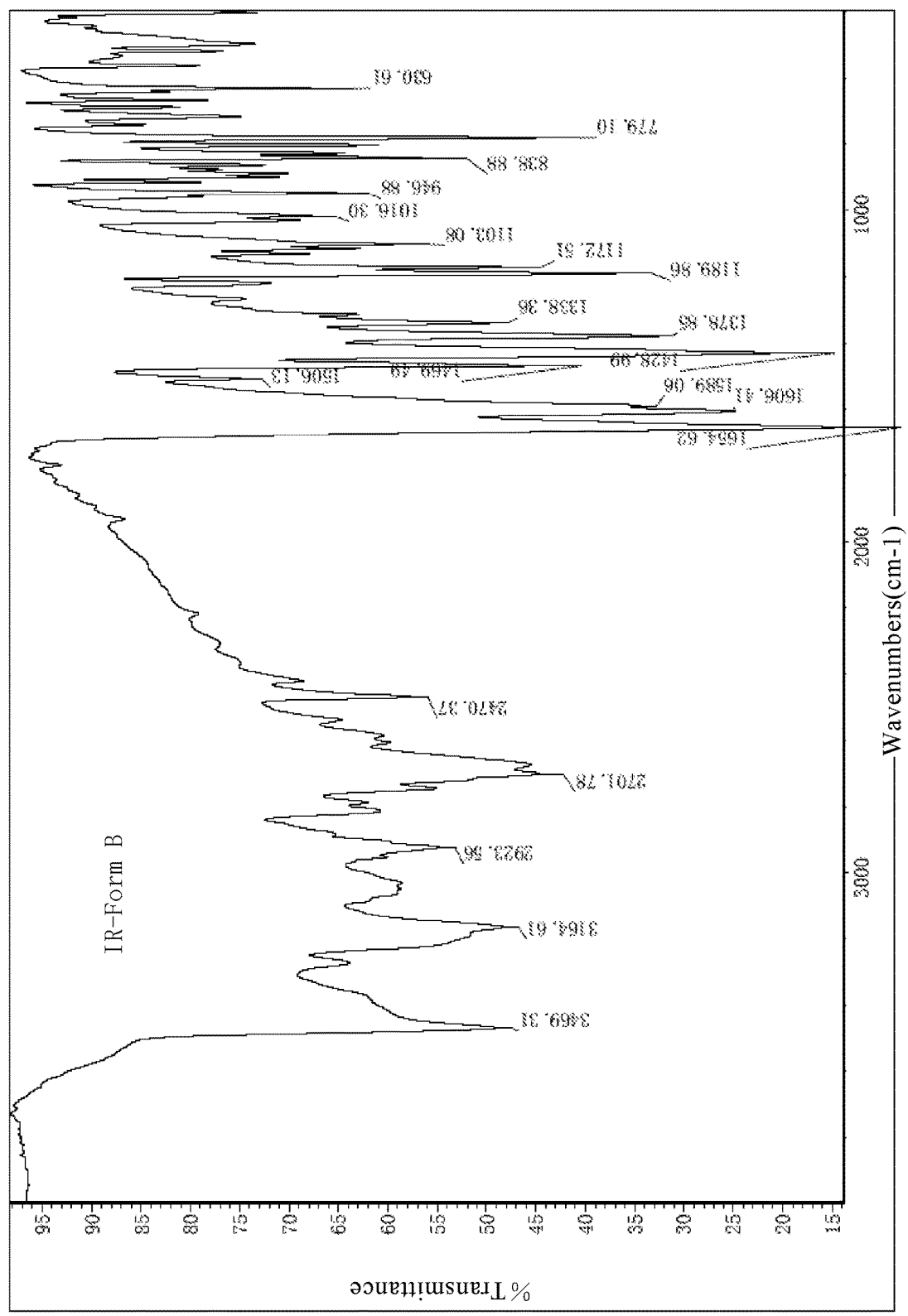
FIG. 2c is an infrared (IR) spectrum of mefurapine hydrochloride crystal form B.

It can be seen from FIG. 2c that, in the infrared spectrum of the crystal form B, there are characteristic peaks at least at 3469 $cm^{-1}$, 3164 $cm^{-1}$, 2923 $cm^{-1}$, 2701 $cm^{-1}$, 2470 $cm^{-1}$, 1654 $cm^{-1}$, 1606 $cm^{-1}$, 1589 $cm^{-1}$, 1428 $cm^{-1}$, 1469 $cm^{-1}$, 1428 $cm^{-1}$, 1378 $cm^{-1}$, 1338 $cm^{-1}$, 1189 $cm^{-1}$, 1172 $cm^{-1}$, 1103 $cm^{-1}$, and 779 $cm^{-1}$, and the error range is ±2 $cm^{-1}$.

Figure 2D:
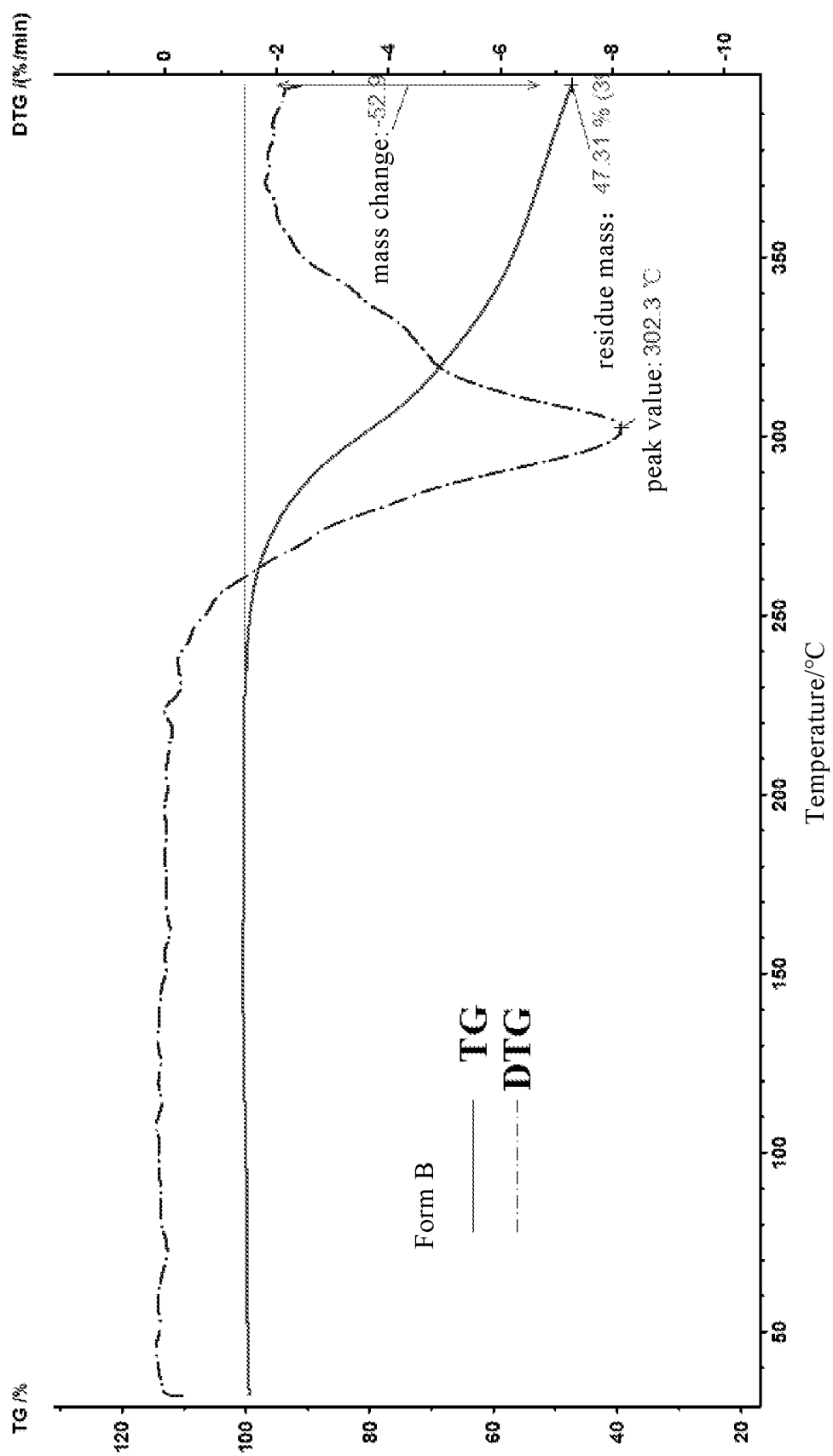
FIG. 2d is a TG spectrum of mefurapine hydrochloride crystal form B.

It can be concluded from FIG. 2*d* that the crystal form B begins to decompose at 250±20° C. according to the thermogravimetric analysis.

Crystal Form C

The powder X-ray diffraction pattern of the mefurapine hydrochloride crystal form C of the present invention has obvious characteristic absorption peaks at diffraction angles (2θ) of approximately 10.306, 12.666, 15.312, 17.436, 18.918, 20.748, 22.974, 24.553, 25.238, 26.241, 29.336, 32.739, 33.738, 34.118, and 35.204.

Figure 3A:
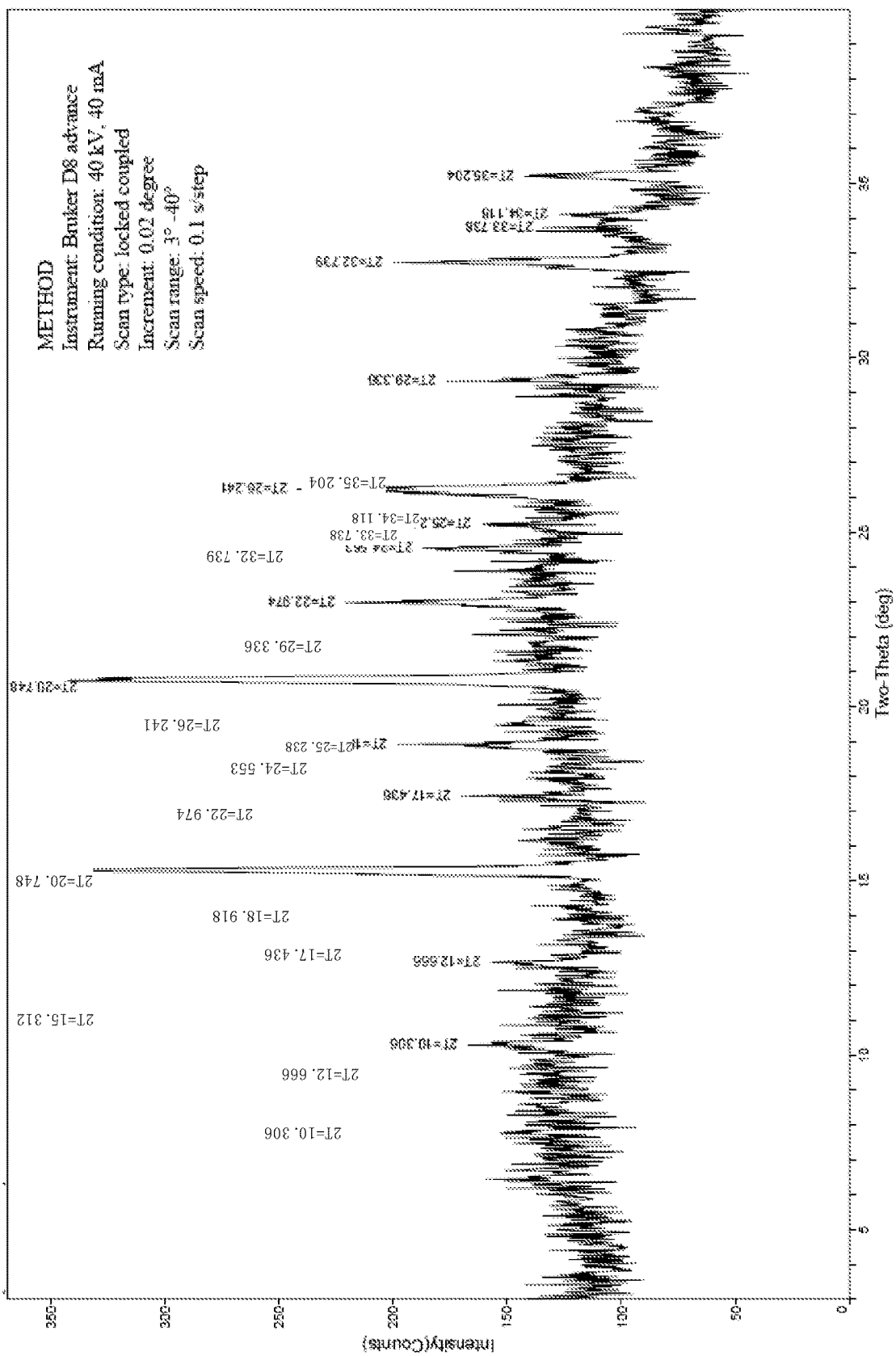
FIG. 3a is an X-ray powder diffraction (XRPD) pattern of mefurapine hydrochloride crystal form C.

The X-ray powder diffraction pattern of the mefurapine hydrochloride crystal form C is substantially consistent with FIG. 3*a*; and the DSC spectrum, the infrared spectrum, the TG spectrum, and the Raman spectrum are substantially consistent with FIGS. 3*b*, 3*c*, 3*d*, and 3*e*.

Figure 3B:
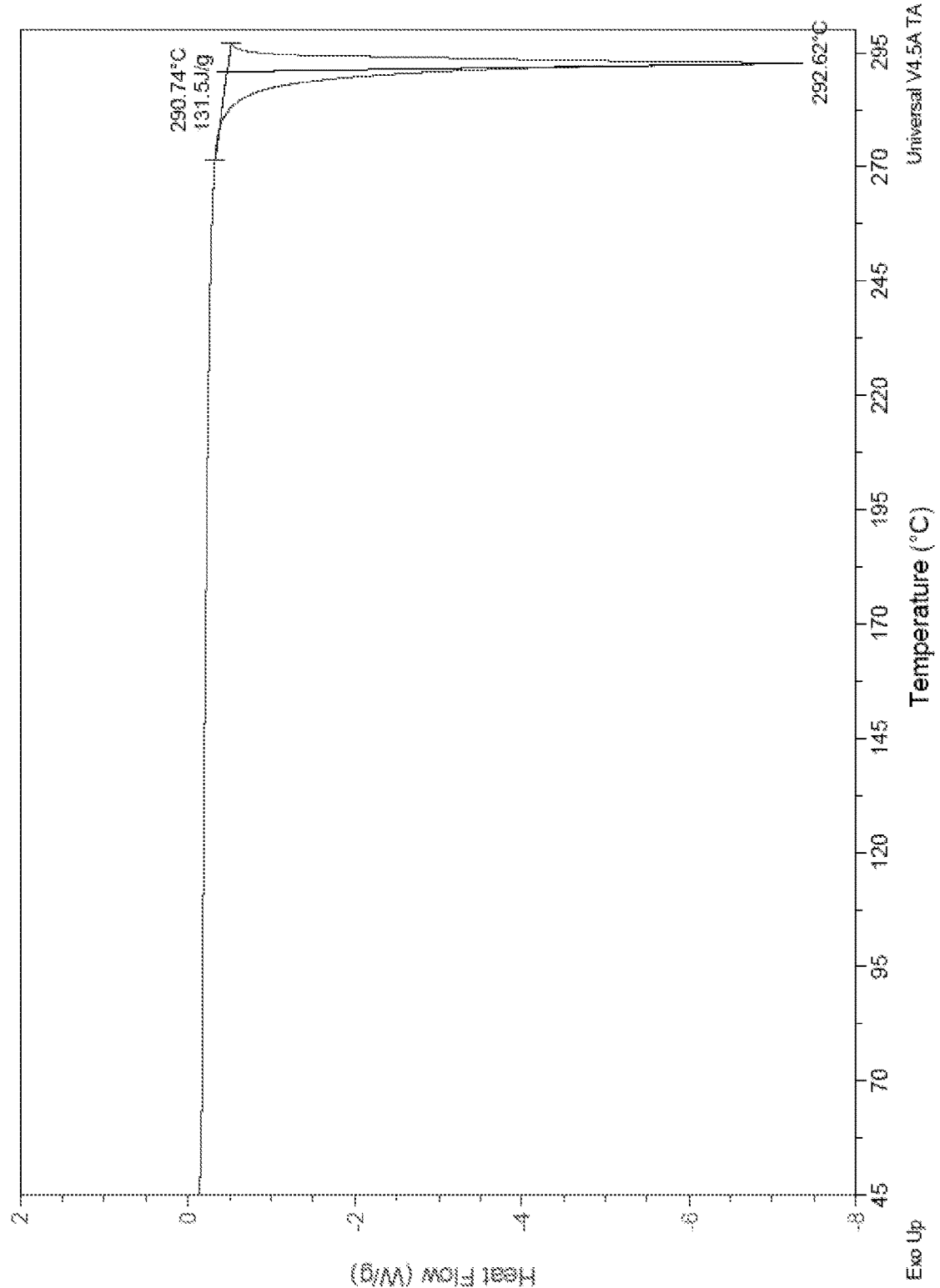
FIG. 3b is a DSC spectrum of mefurapine hydrochloride crystal form C.

It can be seen from FIG. 3*b* that the crystal form C has a characteristic endothermic peak in the range of about 270-300° C.

Figure 3C:
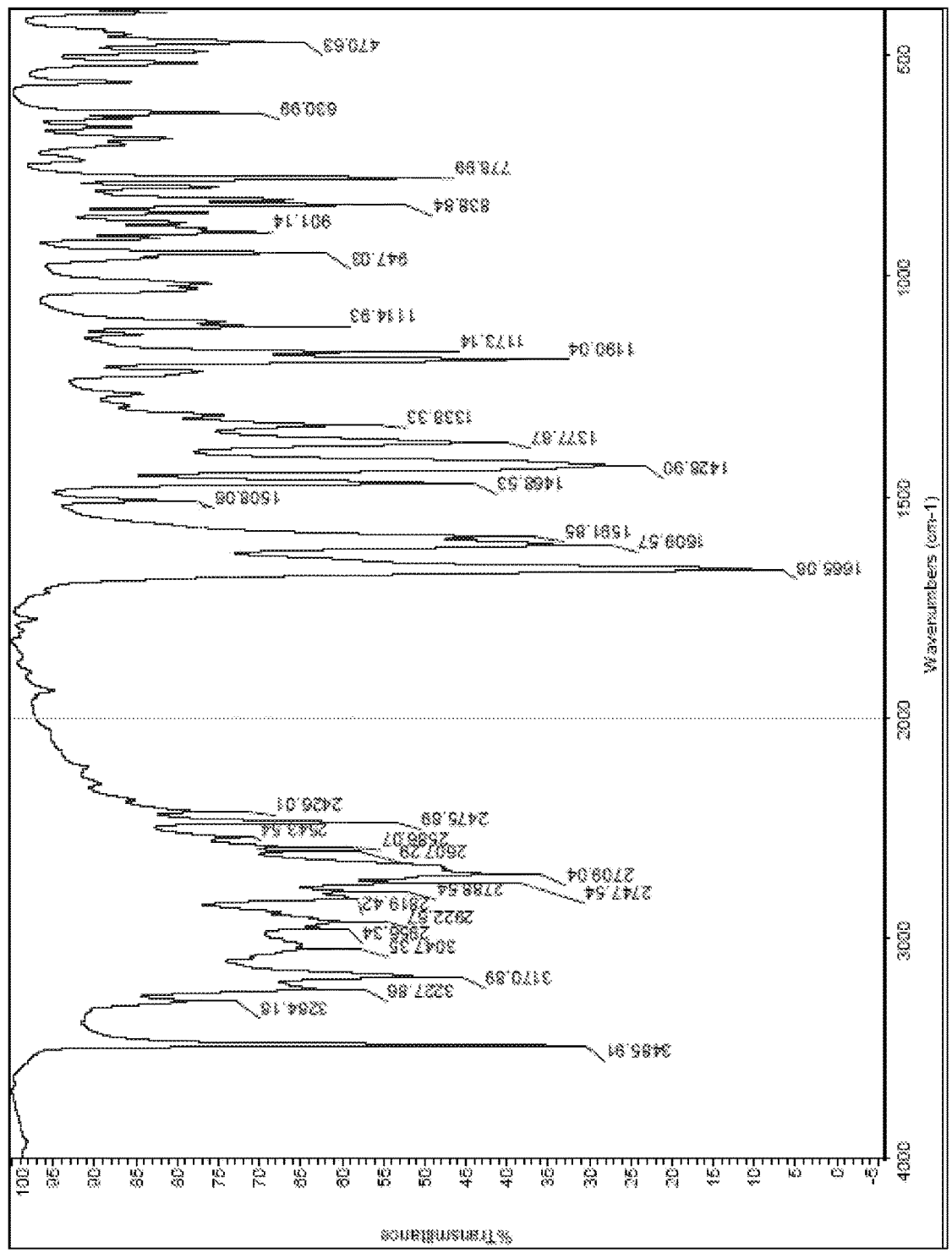
FIG. 3c is an infrared (IR) spectrum of mefurapine hydrochloride crystal form C.

It can be seen from FIG. 3*c* that, in the infrared spectrum of the crystal form C, there are characteristic peaks at least at 3485 $cm^{-1}$, 3227 $cm^{-1}$, 3170 $cm^{-1}$, 3047 $cm^{-1}$, 2747 $cm^{-1}$, 2709 $cm^{-1}$, 2475 $cm^{-1}$, 1665 $cm^{-1}$, 1609 $cm^{-1}$, 1468 $cm^{-1}$, 1428 $cm^{-1}$, 1377 $cm^{-1}$, 1338 $cm^{-1}$, 1190 $cm^{-1}$, 1173 $cm^{-1}$, 1114 $cm^{-1}$, 947 $cm^{-1}$, 838 $cm^{-1}$, and 779 $cm^{-1}$, and the error range is ±2 $cm^{-1}$.

Figure 3D:
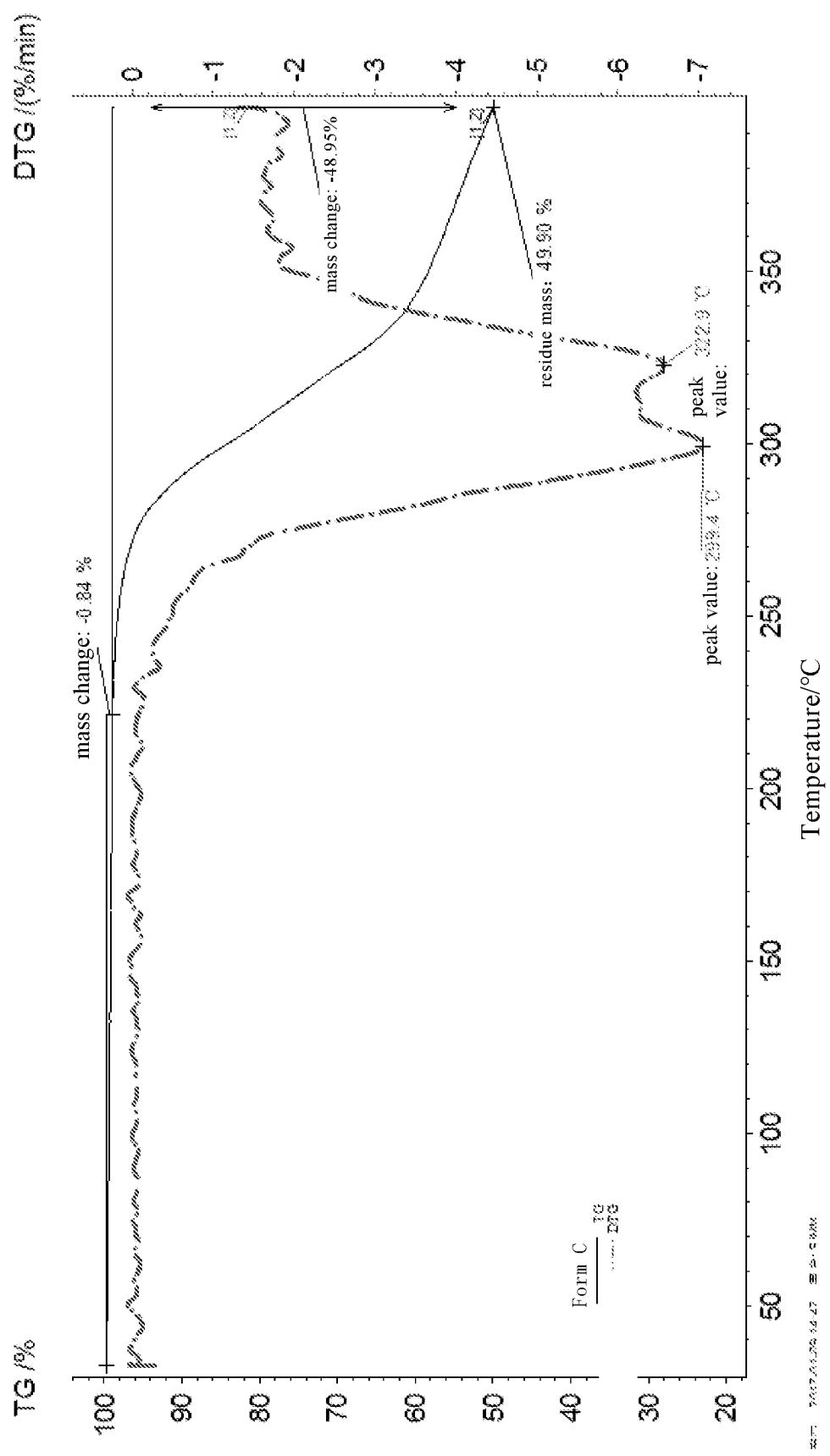
FIG. 3d is a TG spectrum of mefurapine hydrochloride crystal form C.

It can be concluded from FIG. 3*d* that the crystal form C begins to decompose at 250±20° C. according to the thermogravimetric analysis.

From the above experimental results, it can be seen that the crystal forms A, B and C of the present invention have high crystallinity and good thermal stability.

Preparation Method of the Polymorph

The invention also provides a method for preparing the three mefurapine hydrochloride crystal forms A, B and C, and the specific steps are as follows.

Preparation of Mefurapine Hydrochloride Crystal Form A

Mefurapine in free form is dissolved in an organic solvent, HCl/organic solvent is slowly added dropwise at an equivalent ratio, stirred to precipitate solids, which are filtered and dried to obtain mefurapine hydrochloride crystal form A; wherein the organic solvent may be one or more of methanol, ethanol, dichloromethane, ethyl acetate, tetrahydrofuran, and acetone.

Preparation of Mefurapine Hydrochloride Crystal Form B

Mefurapine hydrochloride crystal form A is dissolved in methanol or ethanol, an organic solvent that is highly insoluble to the raw materials is slowly added dropwise, stirred and left to stand. The solution is filtered, and the solid part is dried at 25 degrees to obtain mefurapine hydrochloride crystal form B.

The organic solvent that is highly insoluble to the raw materials is any one or a combination of two or more of butanone, methyl tert-butyl ether, and isopropyl acetate, and preferably butanone or methyl tert-butyl ether, more preferably butanone.

Preparation of Mefurapine Hydrochloride Crystal Form C

Mefurapine hydrochloride crystal form A is completely dissolved in an alcohol or an alcohol-water system, the pH is adjusted to be acidic with hydrochloric acid, and the mixture is stirred at room temperature, and filtered to obtain white solids of mefurapine hydrochloride crystal form C, wherein the alcohol is methanol, ethanol, propanol, tert-butanol, butanol, octanol, pentanol, hexanol, heptanol, decanol, etc., preferably methanol or ethanol, more preferably ethanol.

The alcohol-water system is methanol-water, ethanol-water, propanol-water, tert-butanol-water, butanol-water, octanol-water, pentanol-water, hexanol-water, heptanol-water or decanol-water, etc., preferably methanol-water or ethanol-water system, more preferably ethanol-water system;

The pH is adjusted to 1 to 5, preferably the pH is 2 to 4, more preferably the pH is 2.

Pharmaceutical Composition

The pharmaceutical composition of the present invention contains mefurapine hydrochloride polymorphs in a safe and effective amount range, that is, crystal form A, crystal form B and crystal form C, and pharmacologically acceptable salts thereof and pharmacologically acceptable excipients or carriers, in which, "safe and effective amount" means that the amount of the compound is sufficient to significantly improve the condition without causing serious side effects.

"Pharmaceutically acceptable carrier" means one or more compatible solid or liquid fillers or gelatinous materials which are suitable for human use and should be of sufficient purity and sufficiently low toxicity. "Compatible" means that each component in the composition can be admixed with the polymorph of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

The polymorphs of the invention are usually mixed with at least one conventional inert excipient (or carrier), such as sodium citrate or dicalcium phosphate, or mixed with any of the following components: (a) fillers or compatibilizer, for example, starch, lactose, sucrose, glucose, mannitol and silicic acid; (b) binders, for example, hydroxymethyl cellulose, alginate, gelatin, polyvinylpyrrolidone, sucrose and arabic gum; (c) humectants, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, calcium stearate, magnesium stearate, solid polyethylene glycol, sodium lauryl sulfate, or the mixture thereof. In capsules, tablets and pills, the dosage forms may also contain buffering agents.

Preferably, the excipient includes one or more of a filler, a disintegrant, a binder, and a lubricant.

Preferably, the filler is any one or a combination of starch, lactose, microcrystalline cellulose, dextrin, mannitol, oxidase, and calcium sulfate.

Preferably, the disintegrant includes any one or several of carboxymethylcellulose and salts thereof, crosslinked carboxymethylcellulose and salts thereof, crosslinked povidone, sodium carboxymethyl starch, low substituted hydroxypropylcellulose.

Preferably, the binder includes any one or more of povidone, hydroxypropylmethyl cellulose, starch slurry, and pregelatinized starch.

Preferably, the lubricant includes any one or more of sodium stearyl fumarate, magnesium stearate, and calcium stearate.

Application

The polymorph of mefurapine hydrochloride according to the present invention is used for preparing a medicament for preventing and/or treating a disease related to poly ADP-ribose polymerase (PARP). It can also be used for preparing a medicament for preventing and/or treating tumors. It can also be used to prepare anti-inflammatory drugs.

Diseases associated with poly ADP-ribose polymerase (PARP) include tumors, inflammation, and topical ischemia-reperfusion-associated diseases such as cardiovascular disease, diabetes, rheumatoid arthritis, endotoxin shock, stroke, and the like. The tumor is a tumor with homologous recombination repair deficiency, that is, a tumor in which BRCA1 or BRCA2 is deleted or mutated, such as ovarian cancer, breast cancer, prostate cancer, gastric cancer, pancreatic cancer, cervical cancer, glioma, Ewing's sarcoma, and the like.

Main advantages of the invention include:

Compared with the prior art, the main advantages of the present invention are:

1. The present invention provides different crystal forms of mefurapine hydrochloride, which can be converted into three crystal forms A, B, and C respectively in different crystalline forms of solvent ratio. The three polymorphs can be readily prepared, and the product has high crystal purity and good stability and is easy to be stored.

2. The preparation method of the three polymorphs of the present invention has advantages of simple preparation process, easy operation, good process repeatability, and high purity of the obtained product crystal form.

In order to make the objectives, technical solutions, and advantages of the present invention clearer, the present invention is further described in detail below with reference to the accompanying drawings and embodiments. It should be understood that the specific embodiments described herein are only used to explain the present invention and are not intended to limit the present invention. The experimental methods with no specific conditions described in the following examples are generally performed under the conventional conditions, or according to the manufacture's instructions. Unless otherwise stated, percentages and parts are percentages by weight and parts by weight.

The experimental materials and reagents used in the following examples can be obtained from commercial sources unless otherwise specified.

Experimental conditions:

1) XRPD Method

Instrument model: Bruker D8 advance, target: Cu Kα (40 kV, 40 mA), sample distance to the detector is 30 cm, scanning range is 3°-40° (2 theta value), scanning step: 0.1. It should be noted that, in the powder sample X-ray diffraction pattern, the crystal form with the specific diffraction pattern obtained from the crystalline compound is often characteristic, and the relative intensity of the band (especially at low angles) may change due to dominant orientation effects caused by differences of crystallization conditions, particle size, relative content of the mixture, and other test conditions. Therefore, the relative intensity of the diffraction peaks is not characteristic for the crystals. Whether a crystal form is the same as a known crystal form, it is more important to pay attention to the position of the peaks rather than their relative intensity. In addition, to judge whether the crystal forms are the same, we should pay attention to maintaining the overall concept, because not one diffraction line represents one phase, but a specific set of "d–1/11" data represents a certain phase. It should also be noted that in the identification of mixtures, due to factors such as reduced content, some of the diffraction lines will be missing. At this time, there is no need to rely on the safety band observed in the high-purity sample, and even a band may be characteristic for certain crystals.

2) DSC method Instrument model: Perkin Elmer DSC 8500, temperature range is 50-280° C., scan rate is 10° C./min, and nitrogen flow rate is 50 ml/min.

3) IR method Nicolot-Magna FT-IR750 infrared spectrometer from Nicol Corporation US is used to detect at room temperature, and the detection range is 4000-350 $cm^{-1}$ wave number.

4) TGA method Instrument model: Netzsch TG 209F3, temperature range 30-400° C., scan rate 10K/min, purge gas flow rate 25 mL/min, shielding gas flow rate 15 mL/min.

5) Raman Method Instrument Model: Thermo Scientific, DXR Raman Microscope; Laser power level: 150.0 mW, Filter: 780 nm, Spectrograph aperture: 25 slit-25, Exposure time: 1.00 sec, Number of exposures: 10, Number of background exposures: 32).

6) DVS method Instrument model: SMS DVS Intrinsic, 0~95% RH, temperature: 25° C.

Example 1

Preparation method of crystal form A:

Free mefurapine hydrochloride (59.6 g, 199.9 mmol, purity greater than 97%) was added to methanol/dichloromethane (v/v=1:1, 2000 mL) and stirred vigorously. The solid was not completely dissolved to make the system be a suspension system, cooled to 0° C., and 8N hydrochloric acid in ethyl acetate (250 mL) was slowly added dropwise, and the system was completely dissolved. Upon dropwise addition, the reaction system was continuously stirred at 0° C. to 10° C. for 12 hours, and a large amount of solids precipitated, and filtered to obtain a filter cake. The filter cake was dried under vacuum at 50° C. to 55° C. to constant weight to obtain crystal form A.

The X-ray powder diffraction measurement showed that the obtained crystal form was mefurapine hydrochloride crystal form A. The specific peak positions are shown in Table 1 (see FIG. 1a):

TABLE 1

X-Ray Powder Diffraction (XRPD) Data of mefurapine hydrochloride crystal form A

| 2θ angle/° | d/A | intensity % |
|---|---|---|
| 6.49 | 13.6084 | 15.8 |
| 10.339 | 8.5491 | 9.4 |
| 12.625 | 7.0059 | 11 |
| 15.271 | 5.7972 | 100 |
| 17.395 | 5.094 | 2.8 |
| 18.121 | 4.8914 | 7.8 |
| 18.844 | 4.7053 | 6.5 |
| 19.482 | 4.5526 | 8 |
| 20.727 | 4.2819 | 34.8 |
| 21.448 | 4.1396 | 6.6 |
| 22.933 | 3.8748 | 11.4 |
| 23.133 | 3.8418 | 8.7 |
| 23.913 | 3.7181 | 21.3 |
| 24.5 | 3.6304 | 4.2 |
| 25.139 | 3.5395 | 24.3 |

TABLE 1-continued

X-Ray Powder Diffraction (XRPD) Data of mefurapine hydrochloride crystal form A

| 2θ angle/° | d/Å | intensity % |
|---|---|---|
| 25.618 | 3.4743 | 11.6 |
| 26.082 | 3.4137 | 26.2 |
| 27.084 | 3.2896 | 12.1 |
| 27.406 | 3.2517 | 20.8 |
| 28.828 | 3.0944 | 11.3 |
| 29.31 | 3.0446 | 3.5 |
| 29.891 | 2.9867 | 9.2 |
| 30.591 | 2.9199 | 3.3 |
| 30.789 | 2.9016 | 3.8 |
| 32.717 | 2.7349 | 5 |
| 33.681 | 2.6588 | 5.1 |
| 35.163 | 2.5501 | 3 |
| 35.441 | 2.5307 | 2.1 |
| 35.964 | 2.4951 | 2.9 |
| 36.688 | 2.4475 | 3.5 |
| 37.048 | 2.4245 | 5 |
| 38.132 | 2.3581 | 1.3 |
| 39.375 | 2.2865 | 3.6 |
| 40.075 | 2.2481 | 1.8 |
| 40.68 | 2.216 | 2.7 |
| 43.606 | 2.0739 | 1.4 |
| 43.926 | 2.0596 | 1.4 |

Other tests were performed on the obtained samples, and the obtained DSC spectrum, infrared spectrum, TG spectrum, and Raman spectrum were substantially consistent with FIGS. 1b, 1c, 1d, and 1e.

Example 2

Preparation method of crystal form A:

About 25 mg of 2-[4-(methylaminomethyl)phenyl]-5-fluoro-benzofuran-7-carboxamide hydrochloride of Example 1 was taken, and stirred with 1 ml of methanol at 25° C. for at least 24 h. Then, the solution was filtered, and the solid part was dried in air for 10 min, and then XRPD detection was performed. The results of the X-ray powder diffraction data are shown in Table 1.

Example 3

Preparation method of crystal form A:

The difference from Example 2 is that the solvent was replaced with ethanol, and the results of the X-ray powder diffraction data are shown in Table 1.

Example 4

Preparation method of crystal form A:

The difference from Example 2 is that the solvent was replaced with isopropyl alcohol, and the results of the X-ray powder diffraction data are shown in Table 1.

Example 5

Preparation method of crystal form A:

The difference from Example 2 is that the solvent was replaced with ethyl acetate, and the results of the X-ray powder diffraction data are shown in Table 1.

Example 6

Preparation method of crystal form A:

The difference from Example 2 is that the solvent was replaced with a methanol-water system having a volume ratio of 1:1, and the results of the X-ray powder diffraction data are shown in Table 1.

Example 7

Preparation method of crystal form A

The difference from Example 2 is that the temperature was adjusted to 50° C., and the results of the X-ray powder diffraction data are shown in Table 1.

Example 9

Preparation method of crystal form B:

About 25 mg of 2-[4-(methylaminomethyl)phenyl]-5-fluoro-benzofuran-7-carboxamide hydrochloride of Example 1 was taken, and methanol (3 mL) was added at 25° C. until the raw materials were completely dissolved, and then butanone (12 mL) was slowly added dropwise. Upon dropwise addition, the mixture was stirred at this temperature for 12 hours, and filtered. The filter cake was dried under vacuum at 50° C. to 55° C. to constant weight to obtain crystal form B.

The X-ray powder diffraction measurement showed that the obtained crystal form was mefurapine hydrochloride crystal form B. The specific peak positions are shown in Table 2 (see FIG. 2a).

TABLE 2

X-Ray Powder Diffraction (XRPD) Data of mefurapine hydrochloride crystal form B

| 2θ angle/° | d/Å | intensity % |
|---|---|---|
| 6.145 | 14.37 | 18.6 |
| 10.318 | 8.566 | 16.5 |
| 12.459 | 7.0985 | 12.8 |
| 14.914 | 5.9353 | 100 |
| 15.154 | 5.8418 | 8.5 |
| 17.204 | 5.15 | 3.5 |
| 17.6 | 5.0349 | 5.4 |
| 18.643 | 4.7557 | 6.3 |
| 19.082 | 4.6472 | 6.6 |
| 19.965 | 4.4436 | 3.6 |
| 20.806 | 4.2659 | 51.1 |
| 22.832 | 3.8917 | 10.7 |
| 23.295 | 3.8153 | 10.9 |
| 23.933 | 3.7151 | 4.6 |
| 24.996 | 3.5595 | 30.1 |
| 25.198 | 3.5313 | 42.1 |
| 25.481 | 3.4928 | 11 |
| 25.778 | 3.4532 | 2.5 |
| 26.787 | 3.3254 | 10.8 |
| 27.285 | 3.2658 | 10.4 |
| 28.003 | 3.1836 | 19.8 |
| 29.59 | 3.0165 | 18.2 |
| 31.374 | 2.8488 | 2.7 |
| 32.012 | 2.7935 | 2.1 |
| 32.536 | 2.7497 | 2.4 |
| 32.9 | 2.7202 | 6.3 |
| 33.519 | 2.6713 | 3.2 |
| 33.722 | 2.6556 | 3.6 |
| 35.065 | 2.557 | 2.6 |
| 35.724 | 2.5113 | 9.8 |
| 36.046 | 2.4896 | 5.4 |
| 36.767 | 2.4424 | 3.5 |
| 39.012 | 2.3069 | 6 |
| 39.426 | 2.2836 | 1.7 |

Other tests were performed on the obtained samples, and the obtained DSC spectrum, infrared spectrum, TG spectrum, and Raman spectrum were substantially consistent with FIGS. 2b, 2c, 2d, and 2e.

Example 10

Preparation method of crystal form B:

About 25 mg of 2-[4-(methylaminomethyl)phenyl]-5-fluoro-benzofuran-7-carboxamide hydrochloride of Example 1 was taken, and methanol (1.8 mL) was added at 50° C. until the raw materials were completely dissolved, and then butanone (6 mL) was slowly added dropwise. Upon dropwise addition, the mixture was stirred at this temperature for 12 hours, and filtered. The filter cake was dried under vacuum at 50° C. to 55° C. to constant weight to obtain crystal form B. The results of the X-ray powder diffraction data are shown in Table 2.

Example 11

Preparation method of crystal form C:

About 100 mg of 2-[4-(methylaminomethyl)phenyl]-5-fluoro-benzofuran-7-carboxamide hydrochloride of Example 1 was taken and added to 4 ml of anhydrous ethanol, the temperature was raised to 50° C. with stirring, and then pure water was added and stirred until the raw materials were completely dissolved. The mixture was stirred at this temperature for 30 min, then concentrated hydrochloric acid was added dropwise to adjust the pH to about 2. The mixture was naturally cooled to room temperature, stirred for about 12 hours, and filtered to obtain white solids. The filter cake was rinsed with anhydrous ethanol, suction-filtered, and dried at 50° C.~55° C. under vacuum to constant weight to obtain crystal form C.

The X-ray powder diffraction measurement showed that the obtained crystal form was mefurapine hydrochloride crystal form C. The specific peak positions are shown in Table 3 (see FIG. 3a).

TABLE 3

X-Ray powder diffraction (XRPD) data of mefurapine hydrochloride crystal form C

| 2θ angle/° | d/Å | intensity % |
|---|---|---|
| 10.306 | 8.5765 | 19.2 |
| 12.666 | 6.9831 | 17.9 |
| 15.312 | 5.7817 | 100.0 |
| 17.436 | 5.0820 | 23.3 |
| 18.918 | 4.6870 | 33.8 |
| 20.748 | 4.2776 | 90.0 |
| 22.974 | 3.8679 | 37.1 |
| 24.553 | 3.6226 | 27.1 |
| 25.238 | 3.5259 | 16.7 |
| 26.241 | 3.3934 | 52.1 |
| 29.336 | 3.0419 | 27.1 |
| 32.739 | 2.7331 | 45.0 |
| 33.738 | 2.6544 | 20.4 |
| 34.118 | 2.6257 | 18.8 |
| 35.204 | 2.5472 | 26.7 |

Other tests were performed on the obtained samples, and the obtained DSC spectrum, infrared spectrum, TG spectrum, and Raman spectrum were substantially consistent with FIGS. 3b, 3c, 3d, and 3e.

Example 12

Preparation method of crystal form C:

The difference from Example 10 is that the organic solvent is methanol, and its X-ray powder diffraction data is shown in Table 3.

Example 13

Preparation method of crystal form C:

The difference from Example 10 is that the reaction temperature is 78° C., and its X-ray powder diffraction data is shown in Table 3.

All literatures mentioned in the present invention are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A polymorph of 2-[4-(methylaminomethyl)phenyl]-5-fluoro-benzofuran-7-carboxamide hydrochloride as shown in Formula I,

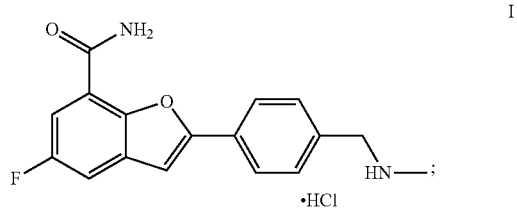 [SMILES: CNCc1ccc(-c2cc3cc(F)cc(C(N)=O)c3o2)cc1 ; Cl]

the polymorph is 2-[4-(methylaminomethyl)phenyl]-5-fluoro-benzofuran-7-carboxamide hydrochloride crystal form A, 2-[4-(methylaminomethyl)phenyl]-5-fluoro-benzofuran-7-carboxamide hydrochloride crystal form B or 2-[4-(methylaminomethyl)phenyl]-5-fluoro-benzofuran-7-carboxamide hydrochloride crystal form C, wherein the powder diffraction pattern of crystal form A comprises 3 or more 2θ values selected from the group consisting of: 6.49±0.1°, 12.625±0.1°, 15.271±0.1°, 20.727±0.1°, 22.933±0.1°, 23.913±0.1°, 25.139±0.1°, 25.618±0.1°, 26.082±0.1°, 27.084±0.1°, 27.406±0.1°, and 28.828±0.1°;

the powder diffraction pattern of crystal form B comprises 3 or more 2θ values selected from the group consisting of: 6.145±0.1°, 10.318±0.1°, 12.459±0.1°, 14.914±0.1°, 20.806±0.1°, 22.832±0.1°, 23.295±0.1°, 24.996±0.1°, 25.198±0.1°, 25.481±0.1°, 26.787±0.1°, 27.285±0.1°, 28.003±0.1°, and 29.59±0.1°;

the powder diffraction pattern of crystal form C comprises 3 or more 2θ values selected from the group consisting of: 10.306±0.1°, 12.666±0.1°, 15.312±0.1°, 17.436±0.1°, 18.918±0.1°, 20.748±0.1°, 22.974±0.1°, 24.553±0.1°, 25.238±0.1°, 26.241±0.1°, 29.336±0.1°, 32.739±0.1°, 33.738±0.1°, 34.118±0.1°, 35.204±0.1°.

Figure 1E:
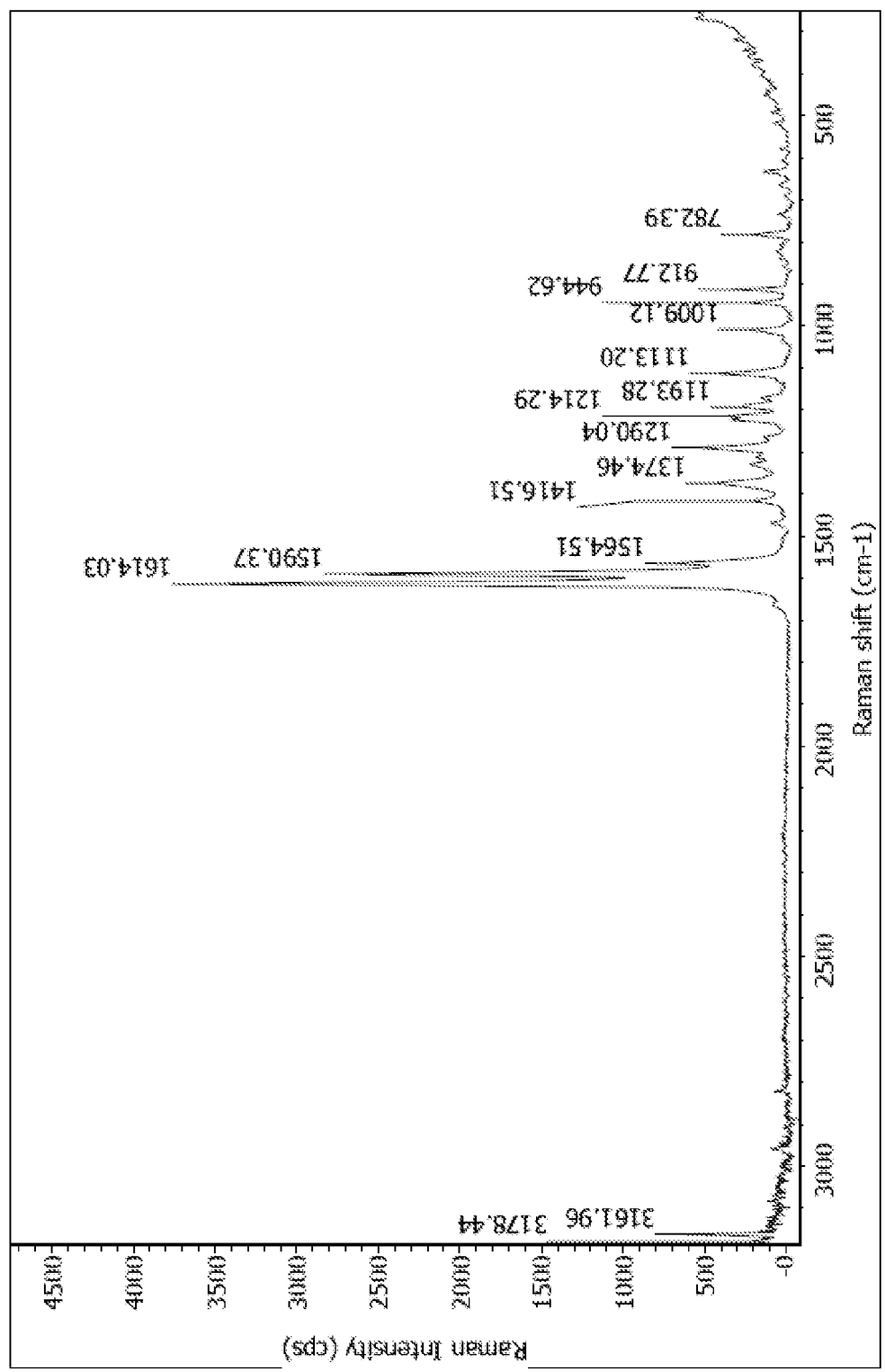
FIG. 1e is a Raman spectrum of mefurapine hydrochloride crystal form A.

2. The polymorph of 2-[4-(methylaminomethyl)phenyl]-5-fluoro-benzofuran-7-carboxamide hydrochloride according to claim 1, wherein the crystal form A further has one or more characteristics selected from the group consisting of:

(1) the crystal form A has a DSC spectrum substantially as shown in FIG. 1b;

(2) the crystal form A has an infrared spectrum substantially as shown in FIG. 1c;
(3) the crystal form A has a TG spectrum substantially as shown in FIG. 1d; and
(4) the crystal form A has a Raman spectrum substantially as shown in FIG. 1e.

Figure 2E:
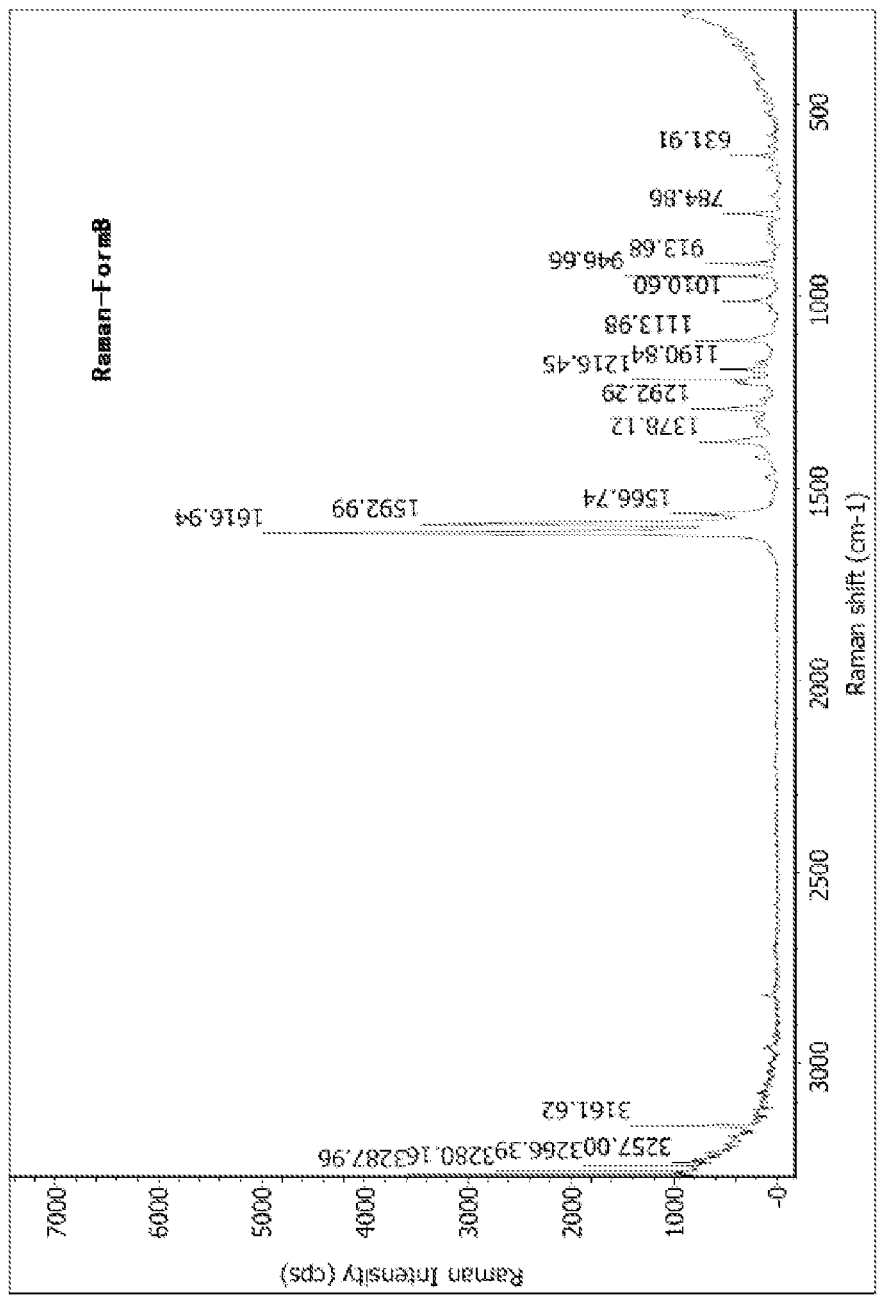
FIG. 2e is a Raman spectrum of mefurapine hydrochloride crystal form B.

3. The polymorph of 2-[4-(methylaminomethyl)phenyl]-5-fluoro-benzofuran-7-carboxamide hydrochloride according to claim 1, wherein the crystal form B further has one or more characteristics selected from the group consisting of:
(1) the crystal form B has a DSC pattern substantially as shown in FIG. 2b;
(2) the crystal form B has an infrared spectrum substantially as shown in FIG. 2c;
(3) the crystal form B has a TG pattern substantially as shown in FIG. 2d; and
(4) the crystal form B has a Raman spectrum substantially as shown in FIG. 2e.

Figure 3E:
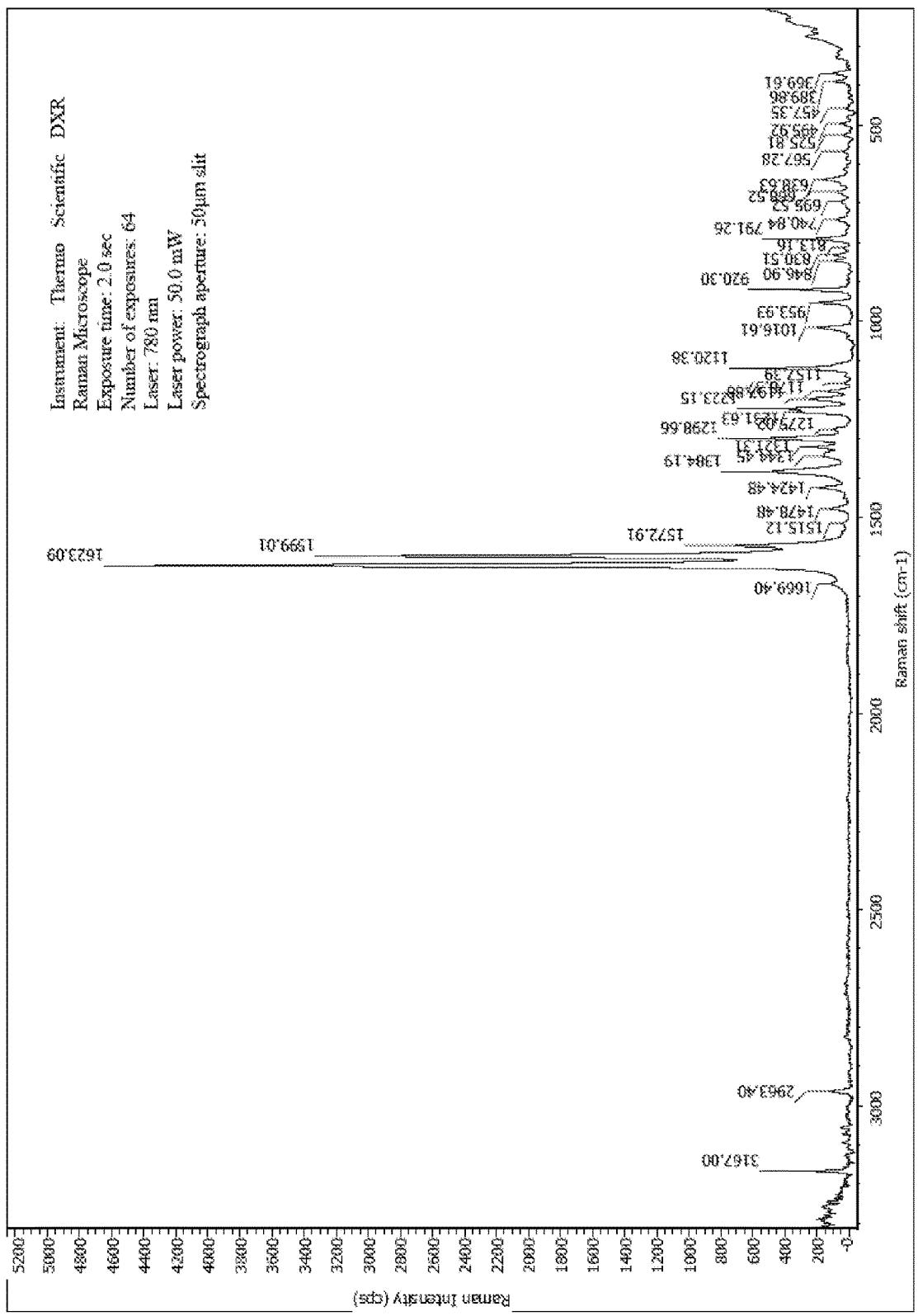
FIG. 3e is a Raman spectrum of mefurapine hydrochloride crystal form C.

4. The polymorph of 2-[4-(methylaminomethyl)phenyl]-5-fluoro-benzofuran-7-carboxamide hydrochloride according to claim 1, wherein the crystal form C further has one or more characteristics selected from the group consisting of:
(1) the crystal form C has a DSC pattern substantially as shown in FIG. 3b;
(2) the crystal form C has an infrared spectrum substantially as shown in FIG. 3c;
(3) the crystal form C has a TG pattern substantially as shown in FIG. 3d; and
(4) the crystal form C has a Raman spectrum substantially as shown in FIG. 3e.

5. A method for preparing the polymorph of 2-[4-(methylaminomethyl)phenyl]-5-fluoro-benzofuran-7-carboxamide hydrochloride according to claim 1, comprising the steps of:
(i) dissolving 2-[4-(methylaminomethyl)phenyl]-5-fluoro-benzofuran-7-carboxamide hydrochloride crystal form A in an alcohol at 0° C. to 80° C. to form an alcohol solution containing 2-[4-(methylaminomethyl)phenyl]-5-fluoro-benzofuran-7-carboxamide hydrochloride;
(ii) adding an organic solvent dropwise to the alcohol solution of step i), stirring, standing, and precipitating crystals; and
(iii) isolating and drying the precipitated crystals to obtain 2-[4-(methylaminomethyl)phenyl]-5-fluoro-benzofuran-7-carboxamide hydrochloride crystal form B;

wherein said alcohol is selected from the group consisting of: methanol, ethanol, propanol, tert-butanol, butanol, octanol, pentanol, hexanol, heptanol, decanol, or a combination thereof; the organic solvent is selected from the group consisting of: butanone, methyl tert-butyl ether, isopropyl acetate, or a combination thereof;

or the preparation method includes the steps of:
(a) dissolving 2-[4-(methylaminomethyl)phenyl]-5-fluoro-benzofuran-7-carboxamide hydrochloride crystal form A in an alcohol or an alcohol-water system at 0° C. to 80° C. to form an alcohol solution or an alcohol-water solution containing 2-[4-(methylaminomethyl)phenyl]-5-fluoro-benzofuran-7-carboxamide hydrochloride;
(b) adjusting the pH of the alcohol solution or the alcohol-water solution of step a) to be acidic with hydrochloric acid, stirring at room temperature, standing, and precipitating crystals; and
(c) separating and drying the precipitated crystals to obtain 2-[4-(methylaminomethyl)phenyl]-5-fluoro-benzofuran-7-carboxamide hydrochloride crystal form C;

wherein said alcohol-water system is selected from the group consisting of methanol-water, ethanol-water, propanol-water, tert-butanol-water, butanol-water, octanol-water, pentanol-water, hexanol-water, heptanol-water or decanol-water.

6. A pharmaceutical composition, characterized in that the composition comprises a pharmaceutically effective dose of the polymorph of 2-[4-(methylaminomethyl)phenyl]-5-fluoro-benzofuran-7-carboxamide hydrochloride according to claim 1, and a pharmaceutically acceptable excipient or carrier.

7. A method for treating diseases related to poly (ADP-ribose polymerase) (PARP) comprising the step of administrating the polymorph of 2-[4-(methylaminomethyl)phenyl]-5-fluoro-benzofuran-7-carboxamide hydrochloride according to claim 1 to a subject in need thereof.

8. A method for treating diseases related to poly (ADP-ribose polymerase) (PARP) comprising the step of administrating the pharmaceutical composition according to claim 6 to a subject in need thereof.

* * * * *